(12) United States Patent
Kartoun et al.

(10) Patent No.: US 11,302,443 B2
(45) Date of Patent: Apr. 12, 2022

(54) SYSTEMS AND METHODS FOR ALERTING ON AMBIGUOUS ADVICE OF MEDICAL DECISION SUPPORT SYSTEMS

(71) Applicant: International Business Machines Corporation, Armonk, NY (US)

(72) Inventors: Uri Kartoun, Cambridge, MA (US); Fang Lu, Billerica, MA (US); Francis Campion, Westwood, MA (US); Kenney Ng, Arlington, MA (US)

(73) Assignee: International Business Machines Corporation, Armonk, NY (US)

( * ) Notice: Subject to any disclaimer, the term of this patent is extended or adjusted under 35 U.S.C. 154(b) by 87 days.

(21) Appl. No.: 16/284,651

(22) Filed: Feb. 25, 2019

(65) Prior Publication Data

US 2020/0273572 A1    Aug. 27, 2020

(51) Int. Cl.
*G16H 50/20* (2018.01)
*G16H 70/40* (2018.01)
(Continued)

(52) U.S. Cl.
CPC ............. *G16H 50/20* (2018.01); *G06F 40/30* (2020.01); *G06N 20/00* (2019.01); *G16H 10/60* (2018.01); *G16H 70/40* (2018.01)

(58) Field of Classification Search
CPC ........ G16H 50/20; G16H 10/60; G16H 70/40; G06N 20/00; G06F 40/30
See application file for complete search history.

(56) References Cited

U.S. PATENT DOCUMENTS 8,954,339 B2    10/2015  Schaffer
10,133,727 B2 *  11/2018  Karres ................... G06F 19/00
(Continued)

FOREIGN PATENT DOCUMENTS

EP          3007771 B1 *   9/2017    ............. G16H 50/20
WO    WO-2009103156 A1 *  8/2009    ............. G16H 20/70

OTHER PUBLICATIONS

Al-Kaysi et al., Predicting tDCS treatment outcomes of patients with major depressive disorder using automated EEG classification, 208 J of Affective Disorders 597-603 (Year: 2017).*
(Continued)

*Primary Examiner* — Evangeline Barr
*Assistant Examiner* — Jordan L Jackson
(74) *Attorney, Agent, or Firm* — Troutman Pepper Hamilton Sanders LLP (57) ABSTRACT

A system and associated method for alerting to ambiguous medical advice through a data analysis system connected to one or more data sources and a client terminal. The data analysis system has an extraction system, a machine learning system, a categorization system, and an alerting system. The data analysis system extracts first information related to outcomes of one or more medical treatments from one or more first data sources, extracts second information related to outcomes of one or more medical treatments from one or more second data sources, and applies machine learning to the extracted first information and second information to develop a classifier for categorizing proposed treatments. The data analysis system also categorizes a proposed treatment or a combination of treatments as potentially harmful based on the classifier, and provides an alert to a client terminal regarding the proposed treatment.

14 Claims, 6 Drawing Sheets

(51) Int. Cl.
*G06N 20/00* (2019.01)
*G16H 10/60* (2018.01)
*G06F 40/30* (2020.01)

(56) References Cited

U.S. PATENT DOCUMENTS

| | | | |
|---|---|---|---|
| 10,552,931 B2* | 2/2020 | Sheffer | G06Q 50/22 |
| 2012/0303388 A1* | 11/2012 | Vishnubhatla | G16H 20/13 |
| | | | 705/3 |
| 2014/0032221 A1 | 1/2014 | Vetter et al. | |
| 2014/0181128 A1* | 6/2014 | Riskin | G06F 16/3344 |
| | | | 707/756 |
| 2015/0356252 A1 | 10/2015 | Beker | |
| 2017/0286622 A1 | 5/2017 | Cox et al. | |
| 2018/0330824 A1* | 11/2018 | Athey | G16B 20/00 |

OTHER PUBLICATIONS

Gilozzo et al., Building Cognitive Applications with IBM Watson Services: vol. 1 Getting Started, IBM Redbooks (Jun. 2017) (Year: 2017).*

Elizabeth O'Dowd, IBM Watson Artificial Intelligence Improves Cancer Treatment, HIT Infrastructure Xtelligent Healthcare Media Storage News (Feb. 1, 2017) (Year: 2017).*

Jo Cavallo, How Watson for Oncology Is Advancing Personalized Patient Care, The ASCO Post (Jun. 25, 2017) (Year: 2017).*

IBM Watson Demo Oncology Diagnosis and Treatment 8 min, YouTube IBMIndiaSS Channel (posted Jan. 6, 2014) (Year: 2014).*

"Harmful Neglect of Decision Support Systems," Althuizen, Reichel, and Wierenga, Decision Support Systems, 54 (2012).

"Clinical Decision Support: a 25 Year Retrospective and a 25 Year Vision" Middleton, Sittig, and Wright, Yearb Med Inform (2016).

* cited by examiner

SYSTEMS AND METHODS FOR ALERTING ON AMBIGUOUS ADVICE OF MEDICAL DECISION SUPPORT SYSTEMS

TECHNICAL FIELD

The present application relates generally to reviewing recommendations or instructions for medical treatment and, more particularly, to alerting on ambiguous or erroneous advice of medical decision support systems.

BACKGROUND

Healthcare organizations and professionals are increasingly using support systems to assist in providing advice to patients. These support systems include medical software tools that automate some of the process of diagnosing patients and making treatment decisions. Such systems can be helpful tools in considering the countless factors that may affect a patient when deciding on a diagnosis and/or recommended course of action. Along with the potential to provide useful decision support that could positively affect a patient's condition, there could be cases in which a proposed decision may be harmful. Examples that illustrate the potential for medical decision support systems to provide ambiguous or erroneous advice can be found in "Harmful Neglect of Decision Support Systems," Althuizen, Reichel, and Wierenga, *Decision Support Systems,* 54 (2012) and "Clinical Decision Support: a 25 Year Retrospective and a 25 Year Vision" Middleton, Sittig, and Wright, *Yearb Med Inform* (2016). These sources include descriptions of instances in which support decisions were not helpful, as evidenced by unacceptably high override rates for a variety of reasons including: outdated patient data, missing patient data, logic that did not precisely fit the patient, clinically irrelevant alerts such as drug-food alerts, or decisioning that came at a point in the clinician's reasoning that was too late (decision already made).

As highlighted in the references cited above, even the most advanced medical decision support systems occasionally provide ambiguous or even erroneous advice to the clinical staff. Such situations pose problems for obvious reasons, as improper or misinformed medical advice is potentially harmful to the patient's health, as well as to the reputation of the clinician and even the software provider. A system that reviews the output of medical decision support systems for potentially problematic advice would therefore enhance and benefit the clinicians and patients that rely on advice from medical decision support systems.

The present disclosure is directed to overcoming these and other problems of the prior art.

SUMMARY

In some embodiments, a computer implemented method for alerting to ambiguous medical advice in a data processing system is disclosed. The data processing system includes a processing device and a memory comprising instructions which are executed by the processor to perform the method. The method includes extracting first information related to outcomes of one or more medical treatments from one or more first data sources, extracting second information related to outcomes of one or more medical treatments from one or more second data sources, and applying machine learning to the extracted first information and second information to develop a classifier for categorizing proposed treatments. The method also includes categorizing a proposed treatment as potentially harmful based on the classifier, and providing an alert to a client terminal regarding the proposed treatment.

In other embodiments, a data analysis system for alerting to ambiguous medical advice from a medical decision support system is disclosed. The data analysis system includes an extraction system for extracting information related to outcomes of one or more medical treatments from one or more publicly-available data sources, a machine learning system for developing a classifier based on the extracted information, a categorization system for categorizing, based on the classifier, proposed treatments output from the medical decision support system, and an alert system for providing alerts on proposed treatments that are categorized as being potentially harmful.

In yet other embodiments, a computer implemented method for alerting to potentially harmful medical advice in a data processing system is disclosed. The data processing system includes a processing device and a memory comprising instructions which are executed by the processor to perform the method. The method includes extracting first information related to undesirable outcomes of one or more medical treatments from one or more publicly-available data sources, extracting second information related to desirable outcomes of one or more medical treatments from one or more other data sources, and applying machine learning to the extracted first information and second information to develop a classifier. The classifier is configured to categorize the accuracy of the desirable outcomes of the one or more medical treatments from the one or more other data sources. The method further includes using the classifier to refine proposed treatments output from a medical decision support system.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF EXEMPLARY EMBODIMENTS

Embodiments of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The present disclosure relates to a system for identifying ambiguous or erroneous advice and alerting relevant parties to the potential of an issue. "Ambiguous or erroneous advice" as used herein may refer to a statement or recommendation that may be incorrect or under-informed due to an unknown or overlooked aspect. In one example, a recommendation to prescribe a particular medication in a situation when a patient is also taking another medication or has another condition may be flagged as ambiguous or erroneous due to a correlation generated and stored within the system based on a review of available information.

The system may be configured to review different sources of information to generate classifications that rate potential advices as reliable or ambiguous or erroneous. The system may use the different sources in a machine learning algorithm to generate the classifier system. In one example, the system receives information from a corpus of documents that includes news sources, legal sources, and scientific sources. There are large numbers of these sources that are rich in valuable information, but the information is so abundant that it is unreasonable for a person to be able to be aware of even a significant portion of it. In another example, the system also receives information from a medical records database.

The system thus is capable of extracting associations from a variety of publicly-available databases that contain information about treatments (such as medications, procedures) that resulted in undesirable outcomes (such as unplanned surgeries, side effects, or even death). These associations may also include combinations of treatments or procedures applied to specific diseases. Such databases or resources include news web sites (e.g., a news article regarding an unsuccessful treatment option), legal-related databases (e.g., a record of a class-action lawsuit regarding a particular medication or use thereof), and scientific literature (e.g., the PubMed website). In some embodiments, these sources may also supply information regarding desirable outcomes (e.g., a news article regarding a new and successful treatment method or pharmaceutical product).

The system collects data and creates a repository that contains associations that are either avoidable, problematic, or harmful. The system includes a decision support system that reviews input information for potentially harmful or problematic content. The decision support system outputs a result related to a review of the information, such as a list of potentially problematic or ambiguous associations. The system provides the associations to a support user. The support user may use those associations and refine the decision support system to avoid proposing potentially harmful advice.

Figure 1:
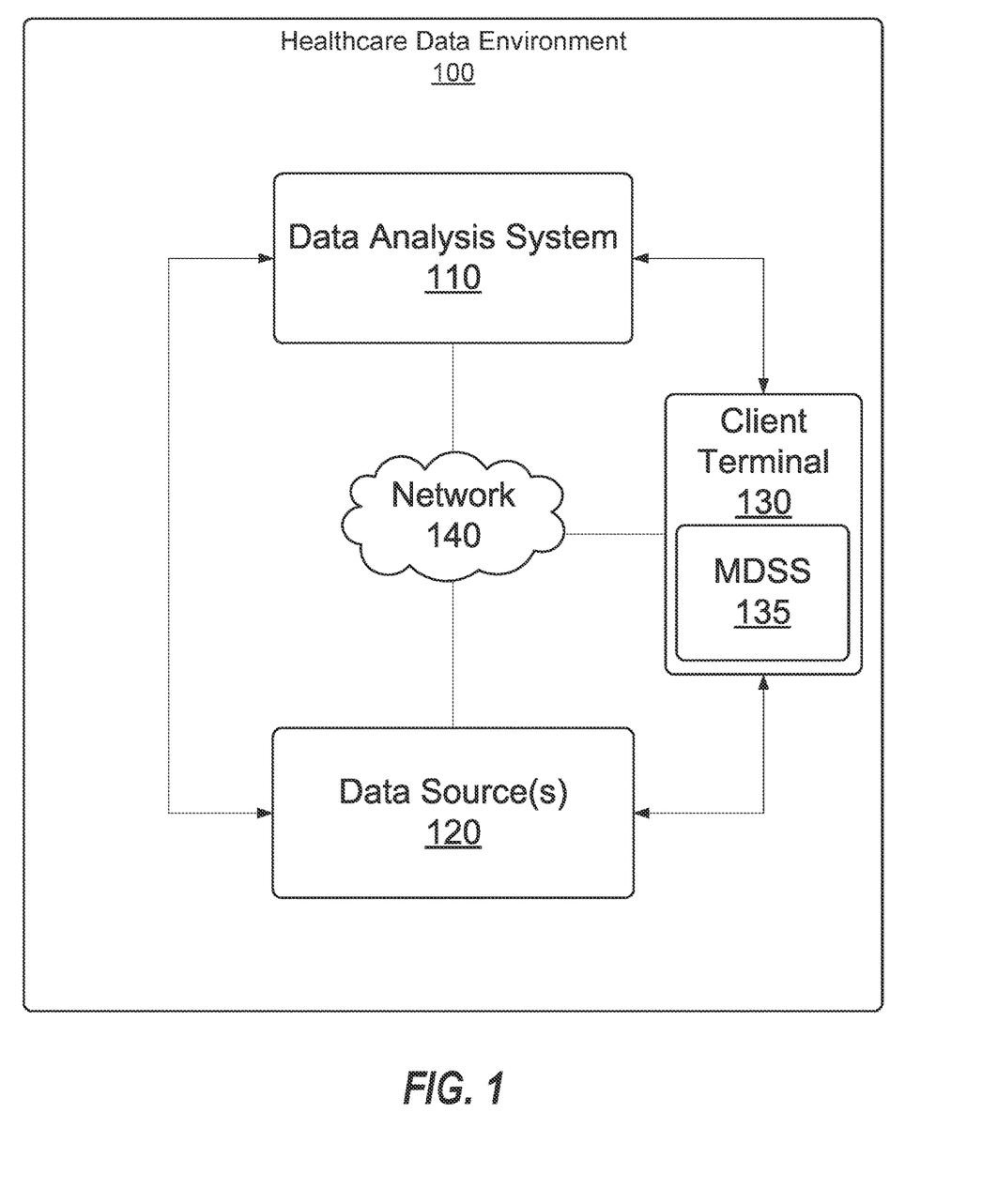
FIG. 1 depicts a block diagram of an exemplary healthcare data environment, consistent with disclosed embodiments.

FIG. 1 is an illustration of an exemplary healthcare data environment 100. The healthcare data environment 100 may include a data analysis system 110, one or more data sources 120, and a client terminal 130. A network 140 may connect the data analysis system 110, the one or more data sources 120, and/or the client terminal 130.

The data analysis system 110 may be a computing device, such as a back-end server. The data analysis system 110 may include components that enable data analysis functions, such as providing output regarding proposed treatments (e.g., a classifier for identifying a proposed treatment as ambiguous, erroneous, effective, reliable, etc.).

The one or more data sources 120 may be computing devices and/or storage devices configured to supply data to the data analysis system 110. In one example, the one or more data sources 120 may include a first data source and a second data source. In some embodiments, the first data source is a corpus of documents containing information regarding undesirable outcomes related to advice. The corpus of documents may include news sources, legal sources, and scientific sources. In this way, the first data source may be associated with publicly-available information. A news article that reports on the outcome of one or more individuals taking a medication that had a harmful side effect due to another coinciding condition (e.g., co-prescribed medication, illness or disease, medical condition, etc.) is potentially relevant to advice that a clinician may provide or believe to be viable. Similar information could be found in other public sources, such as legal databases and/or within scientific literature.

The second data source, on the other hand, may be associated with medical records, such as a medical records database. In this way, the second data source may be associated with private or confidential data. In at least some embodiments, the medical records may provide the data analysis system 110 with information regarding successful treatment options and medical advice (e.g., correlations that result in desirable outcomes) based on actual medical data associated with patients. In some embodiments, the medical records may also provide the data analysis system 110 with undesirable outcomes or correlations. The second data source may therefore serve as a source of data that can be used to "check" the information found in the first data source.

The client terminal 130 may be a computing device, such as a user-end device (e.g., a desktop or laptop computer, mobile device, etc.). The client terminal 130 may communicate with the data analysis system 110 to receive information and provide feedback related to the evaluation of potential or actual medical advice associated with a medical decision support system. In some embodiments, the client terminal 130 may be a computing device storing software associated with a medical decision support system (MDSS) 135 that provides recommendations regarding treatment options to a clinical user.

The network 140 may be a local or global network and may include wired and/or wireless components and functionality which enable internal and/or external communication for components of the healthcare data environment 100. The network 140 may be embodied by the Internet, provided at least in part via cloud services, and/or may include one or more communication devices or systems which enable data transfer to and from the systems and components of the healthcare data environment 100.

In accordance with some exemplary embodiments, the data analysis system 110, data source(s) 120, client terminal 130, or the related components include logic implemented in specialized hardware, software executed on hardware, or any combination of specialized hardware and software executed on hardware, for implementing the order reporting system 100 or related components. In some exemplary embodiments, the data analysis system 110 or any of its components may be or include the IBM Watson™ system available from International Business Machines Corporation of Armonk, N.Y., which is augmented with the mechanisms of the illustrative embodiments described hereafter.

Figure 2:
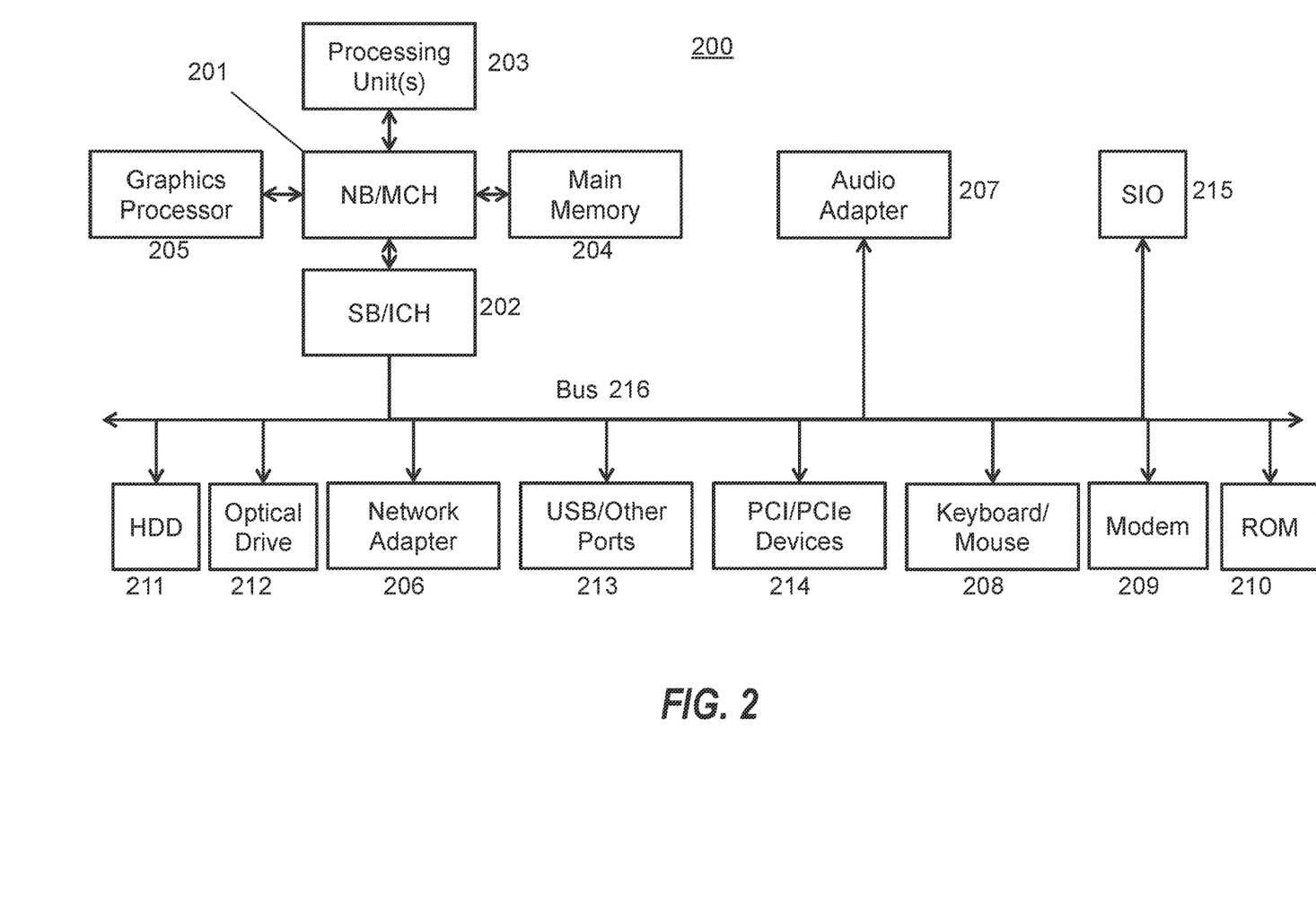
FIG. 2 is a block diagram of an example data processing system in which aspects of the illustrative embodiments are implemented.

FIG. 2 is a block diagram of an example data processing system 200 in which aspects of the illustrative embodiments are implemented. Data processing system 200 is an example of a computer in which computer usable code or instructions implementing the process for illustrative embodiments of the present invention are located. In one embodiment, FIG. 2 represents the data analysis system 110, which implements at least some of the aspects of the healthcare data environment 100 described herein.

In the depicted example, data processing system 200 can employ a hub architecture including a north bridge and memory controller hub (NB/MCH) 201 and south bridge and input/output (I/O) controller hub (SB/ICH) 202. Processing unit 203, main memory 204, and graphics processor 205 can be connected to the NB/MCH 201. Graphics processor 205 can be connected to the NB/MCH 201 through an accelerated graphics port (AGP).

In the depicted example, the network adapter 206 connects to the SB/ICH 202. The audio adapter 207, keyboard and mouse adapter 208, modem 209, read only memory (ROM) 210, hard disk drive (HDD) 211, optical drive (CD or DVD) 212, universal serial bus (USB) ports and other communication ports 213, and the PCI/PCIe devices 214 can connect to the SB/ICH 202 through bus system 216. PCI/PCIe devices 214 may include Ethernet adapters, add-in cards, and PC cards for notebook computers. ROM 210 may be, for example, a flash basic input/output system (BIOS). The HDD 211 and optical drive 212 can use an integrated drive electronics (IDE) or serial advanced technology attachment (SATA) interface. The super I/O (SIO) device 215 can be connected to the SB/ICH 202.

An operating system can run on processing unit 203. The operating system can coordinate and provide control of various components within the data processing system 200. As a client, the operating system can be a commercially available operating system. An object-oriented programming system, such as the Java™ programming system, may run in conjunction with the operating system and provide calls to the operating system from the object-oriented programs or applications executing on the data processing system 200. As a server, the data processing system 200 can be an IBM® eServer™ System p® running the Advanced Interactive Executive operating system or the Linux operating system. The data processing system 200 can be a symmetric multiprocessor (SMP) system that can include a plurality of processors in the processing unit 203. Alternatively, a single processor system may be employed.

Instructions for the operating system, the object-oriented programming system, and applications or programs are located on storage devices, such as the HDD 211, and are loaded into the main memory 204 for execution by the processing unit 203. The processes for embodiments of the website navigation system can be performed by the processing unit 203 using computer usable program code, which can be located in a memory such as, for example, main memory 204, ROM 210, or in one or more peripheral devices.

A bus system 216 can be comprised of one or more busses. The bus system 216 can be implemented using any type of communication fabric or architecture that can provide for a transfer of data between different components or devices attached to the fabric or architecture. A communication unit such as the modem 209 or network adapter 206 can include one or more devices that can be used to transmit and receive data.

Those of ordinary skill in the art will appreciate that the hardware depicted in FIG. 2 may vary depending on the implementation. For example, the data processing system 200 includes several components which would not be directly included in some embodiments of the data analysis system 110. However, it should be understood that a data analysis system 110 may include one or more of the components and configurations of the data processing system 200 for performing processing methods and steps in accordance with the disclosed embodiments.

Moreover, other internal hardware or peripheral devices, such as flash memory, equivalent non-volatile memory, or optical disk drives may be used in addition to or in place of the hardware depicted. Moreover, the data processing system 200 can take the form of any of a number of different data processing systems, including but not limited to, client computing devices, server computing devices, tablet computers, laptop computers, telephone or other communication devices, personal digital assistants, and the like. Essentially, data processing system 200 can be any known or later developed data processing system without architectural limitation.

Figure 3:
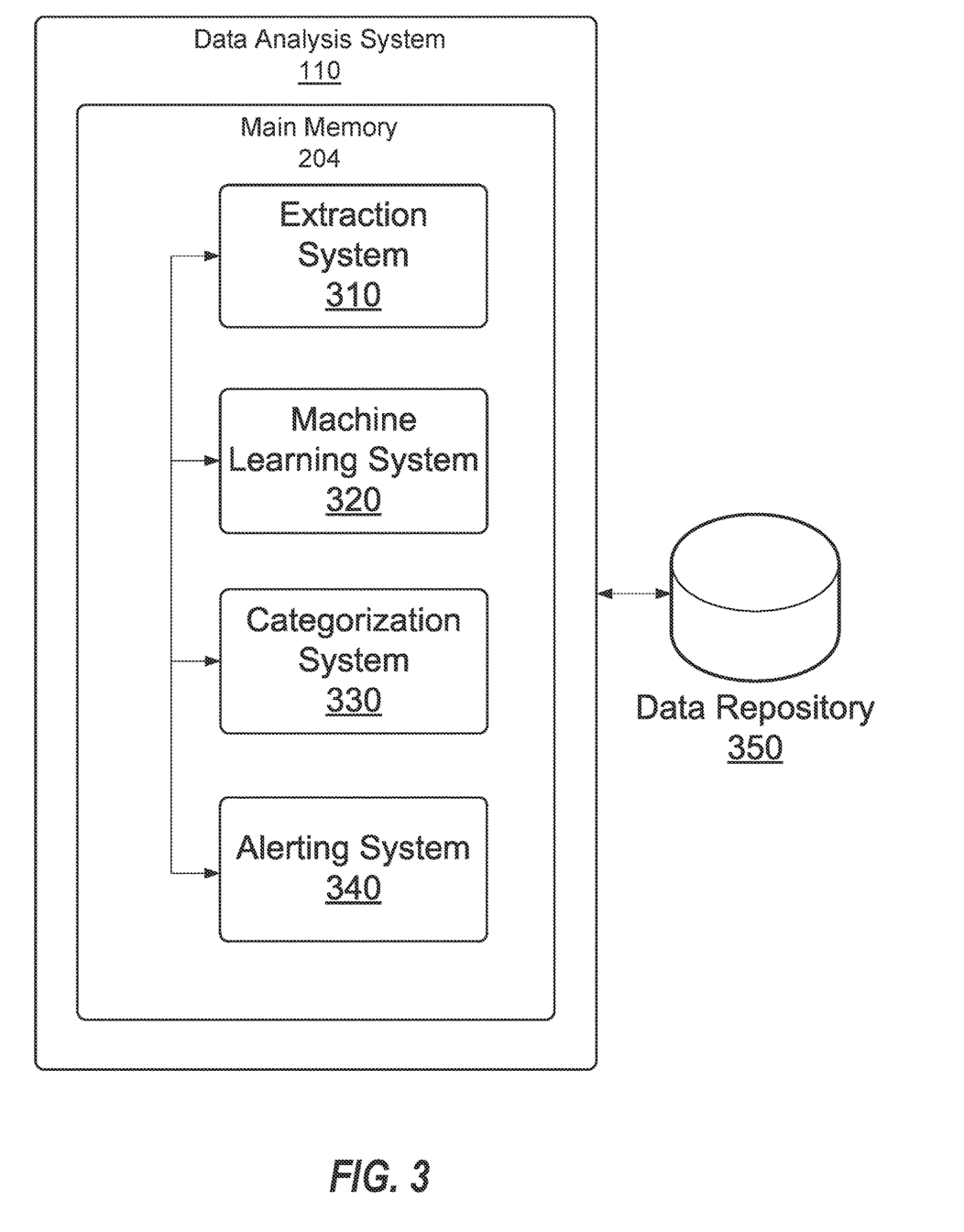
FIG. 3 is a block diagram of an exemplary data analysis system, consistent with disclosed embodiments.

FIG. 3 illustrates an exemplary embodiment of the data analysis system 110. In an exemplary embodiment, the data analysis system 110 includes an extraction system 310, a machine learning system 320, a categorization system 330, and an alerting system 340. These subsystems of the data analysis system 110 may components of a single device, or may be separated devices connected to each other (e.g., via the network 140). In some embodiments, the data analysis system 110 may further include and/or be connected to a data repository 350.

The extraction system 310 may be a computing device or component (e.g., software or hardware engine or module) configured to extract data from the one or more data sources 120. The extraction system 310 may be configured to perform natural language processing on data elements within the one or more data sources 120. The data sources 120 may include data elements such as news articles, legal forms and writings, and scientific literature. The extraction system 310 is configured to perform natural language processing on these and other data elements to extract information that is useful in disclosed processes.

In some embodiments, the extraction system 310 is configured to extract information related to outcomes of one or more medical treatments. For instance, the extraction system 310 may be configured to perform natural language processing of a news article related to an unwanted outcome of a particular medical treatment. In another example, the extraction system 310 may be configured to extract information from medical records to identify effects of medical treatments. For instance, the extraction system 310 may extract laboratory test results and clinical narrative notes from medical records to identify treatment outcomes related to a medical treatment performed or prescribed to a patient.

The machine learning system 320 may be a computing device or component (e.g., software or hardware engine or module) configured to compare sets of extracted information to develop a classifier for rating the correctness of a proposed treatment. In an exemplary embodiment, the classifier generated by the machine learning system 320 is configured to categorize a proposed treatment as ambiguous based on evidence extracted from one or more data sources 120. As used herein, the term "ambiguous" indicates that there should be some caution in proceeding with the proposed treatment, inclusive of situations in which a proposed treatment might be problematic and situations in which a proposed treatment is likely problematic. The machine learning system 320 may be configured to identify a threshold confidence level and rating system for assessing whether a proposed treatment should be considered ambiguous (or some other categorization, such as erroneous, dangerous, reliable, effective, etc.). The machine learning method calculates a probability for a given treatment or a combination of treatments of potentially being harmful. This is achieved, as an example, by scanning a large collection of publicly available narrative sources to evaluate the type of a treatment given and the associated outcomes (whether beneficial or harmful). Many resources propose the benefit of using a certain drug or combination of drugs. However, often on-line resources (either official FDA resources or court-pending cases) indicate that a certain combination may hold a risk (and this should be avoided to be suggested as a treatment, or at least present an alert to the clinicians or to the developers of the decision support system). In one example, a publicly-available source (e.g., a news article or legal filing) may show that a combination of amitriptyline and morphine may hold a risk while a combination of dapagliflozin and metformin may be describing as being relatively safe). The machine learning system 320 may be trained by instances of treatments-effects pulled from the narrative resources (such as amitriptyline+morphine=potentially high probability for being harmful, or dapagliflozin+metformin=low probability for being harmful, etc.). Given a large number of combinations and their rankings of low and high risk serving as a training set, the machine learning mechanism is capable of generalizing such associations and identify potential high risk for any given treatment or a combination of treatments. It should be noted that the process described above can identify potentially harmful associations beyond what is known to the FDA or to the manufacturers of the medications. Such associations may commonly be extracted found in news articles, cases discussed in the courts, scientific literature, or other similar sources.

The categorization system 330 may be a computing device (e.g., software or hardware engine or module) configured to use a classifier developed by the machine learning system 320 to categorize treatments. For example, the categorization system 330 may receive extracted treatments from a medical records data source and evaluate the treatments based on the classifier developed in step 320. In some embodiments, the categorization system is configured to receive a proposed treatment from the client terminal 130, classify the proposed treatment, and provide the proposed treatment to the client terminal 130.

In some embodiments, the categorization system 330 may output a category for a proposed treatment from one or more possible categories options. In some embodiments, the category options may include "potentially harmful," which may encompass any proposed treatment that is ambiguous or erroneous. As discussed with respect to the machine learning system 320, the categorization system 330 may use a confidence or rating system to score a proposed treatment and determine whether the confidence or rating is within an acceptable (or unacceptable) range in determining whether a proposed treatment is potentially harmful. In another example, the machine learning system 320 may produce a finite list of treatments that are considered potentially harmful and the categorization system may compare a proposed treatment to the list to determine whether the proposed treatment is on the list. Treatments that are found on the list may be categorized as potentially harmful while treatments that are not on the list may be categorized as acceptable. This list concept may be expanded to other possible category options, such as a list of effective treatments, dangerous treatments, unknown treatments, etc.

The alerting system 340 may be a computing device (e.g., software or hardware engine or module) configured to provide an alert based on the categorization of a proposed treatment. For instance, the alerting system 340 may provide an alert to the client terminal 130 identifying a proposed treatment that has been identified as potentially harmful. In some embodiments, the alerting system 340 may provide one or more categories from a list of category options for a classified treatment. The client terminal 130 may receive the alert and display or otherwise output the alert to a user.

The data repository 350 may be a database configured to store data. The data repository 350 may be configured to receive data from the extraction system 310 and/or from one or more data sources 120 and store the data according to appropriate storage protocols. In some embodiments, the data repository 350 receives data from the data analysis system 110, such as from the extraction system 310. In other embodiments, the data repository 350 receives data from the one or more data sources 120 and is a data supply for the data analysis system 110.

Figure 4:
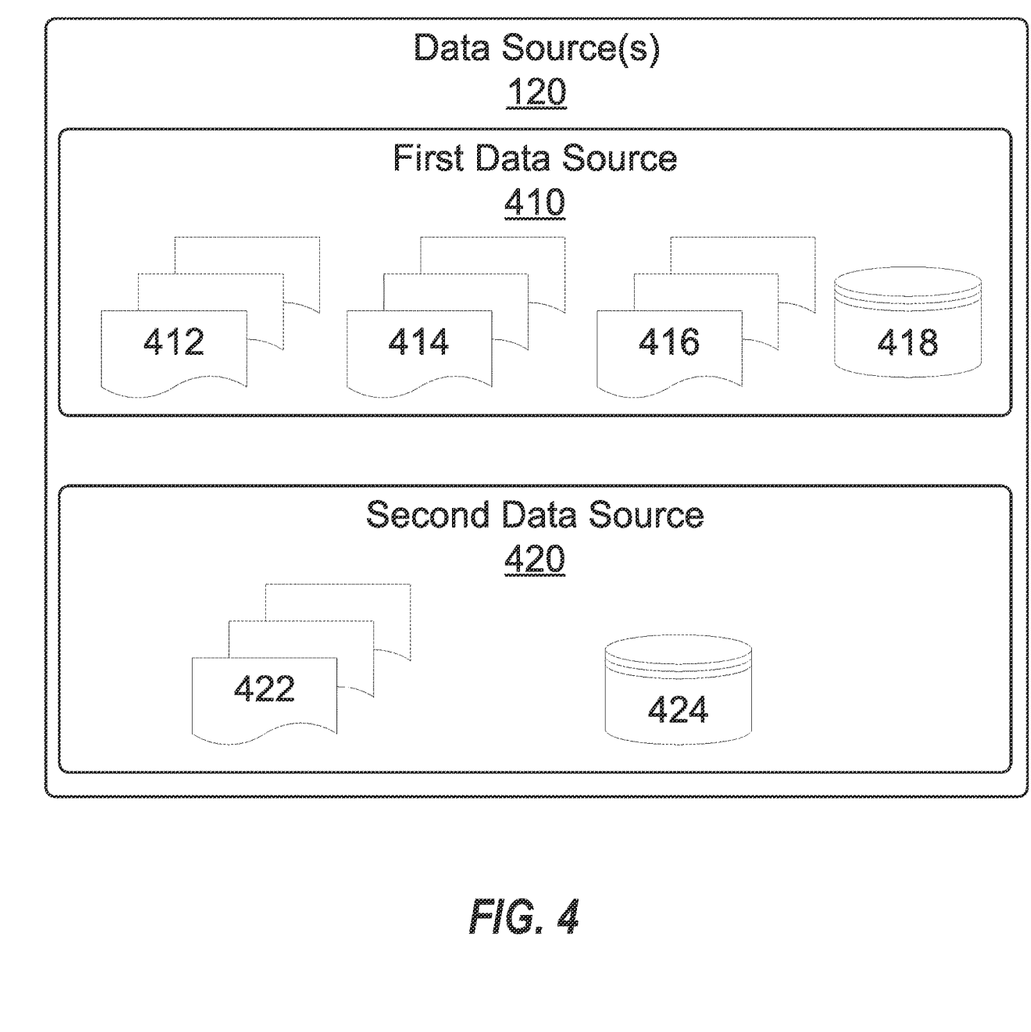
FIG. 4 is a block diagram of a plurality of data sources, consistent with disclosed embodiments.

FIG. 4 is a block diagram of an example of the one or more data sources 120. In one example, the data source(s) 120 include a first data source 410 and a second data source 420. In some embodiments, the first data source 410 and second data source 420 may be data storage elements, such as memory devices or data repositories. While illustrated as separate storage elements, it should be understood that the data may be stored together or separately in different configurations.

In an exemplary embodiment, the first data source 410 and the second data source 420 store information related to outcomes of medical treatments. Examples of medical treatments include procedures, medications, dosages, or other medical advice or instructions. Consistent with disclosed embodiments, medical treatments may include combinations of treatments or conditions, such as the taking of multiple medications, performance of a procedure while taking a medication, dietary advice while a patient has a particular ailment, and the like. and medications (such as effectiveness, side effects, risk factors, etc.). The information related to outcomes of these medical treatments may further include some assessment of the effects, effectiveness, danger, etc. involved in the medical treatment. For example, the information related to outcomes of medical treatments may include data indicating that taking two certain medications at the same time could have dangerous side effects.

In an exemplary embodiment, the first data source 410 includes first information related to outcomes of medical treatments. For instance, the first data source 410 may include a corpus of documents containing one or more of news materials 412, legal materials 414, and scientific materials 416. In one aspect, the first data source 410 therefore includes publicly available information related to the outcomes of medical treatments. In another aspect, the first data source 410 includes information related to undesirable outcomes of medical treatments.

The corpus of documents including news materials 412, legal materials 414, and scientific materials 416 may be aggregated from various locations (e.g., Internet sources, electronically-captured hard copy sources, legal and scientific databases and research tools, etc.) and stored in the database 418. These sources of information may include news reports regarding dangerous treatments, legal documents and opinions discussing the outcomes of treatments that went awry, and/or scientific studies related to treatment outcomes. The extraction system 310 is configured to extract the first information related to outcomes of medical treatments from the first data source 410, such as via natural language processing of the corpus of documents 412-416.

In an exemplary embodiment, the second data source 420 includes second information related to outcomes of medical treatments. For instance, the second data source 420 may include medical records 422, which may be stored in a database 424. The medical records may include patient data for a plurality of patients. The patient data may include any information related to treatment and/or medical advice of the plurality of patients. The patient data may include laboratory test result data, clinical narrative notes, chart data, vitals, demographics, etc. In one aspect, the second data source 420 therefore includes non-public information. In another aspect, the second data source 420 includes information related to desirable outcomes of medical treatments. In some embodiments, the existence of a treatment in the medical records 422 may indicate a desirable outcome of the treatment, considering that the treatment would not have been actually advised if not for the benefit of the patient. In other words, the fact that a treatment is found in the medical records 422 indicates that it is at least possible that the treatment will be proposed again in the future. The extraction system 310 is configured to extract the second information related to outcomes of medical treatments from the second data source 420, such as via natural language process of the medical records 422.

Figure 5:
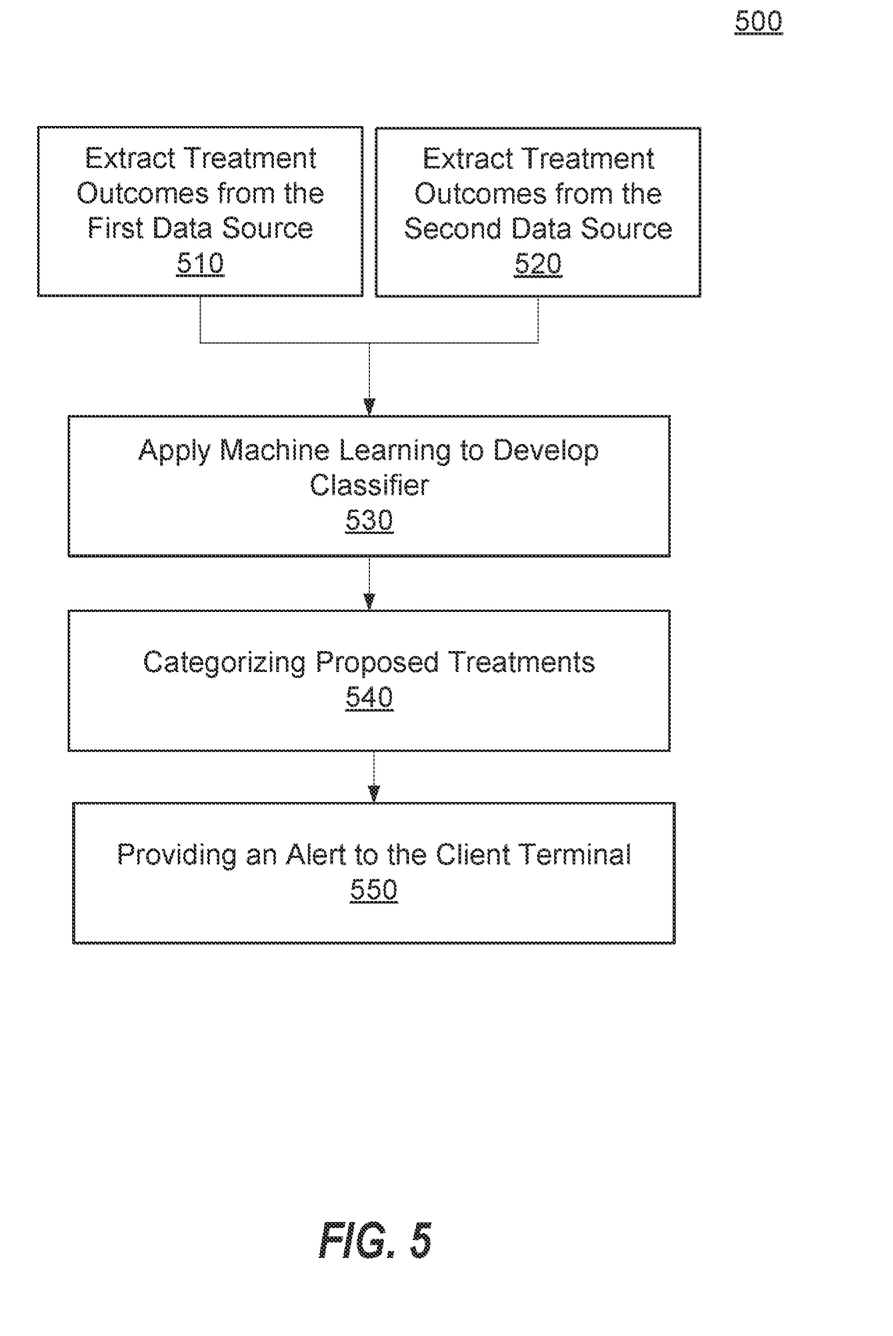
FIG. 5 is a flowchart of an exemplary process for alerting to potentially harmful proposed treatments.

FIG. 5 is a flowchart of an exemplary process for alerting to potentially harmful medical treatments, consistent with disclosed embodiments. The data analysis system 110 may perform one or more steps of the process 500 in order to use information from data source(s) 120 to warn users of potentially harmful treatments before they are advised to a patient and/or proposed by the medical decision support system 135.

In step 510, the extraction system 310 extracts first information related to treatment outcomes from the first data source 410. For instance, the extraction system 310 may perform natural language processing of the corpus of documents 412-416 in order to extract data from the documents. The extracted first information related to treatment outcomes may be associated with, for example, harmful interactions between medications. In this way, the information related to treatment outcomes may identify associations or combinations of treatments and/or conditions that could be problematic or harmful if suggested or allowed to occur. For instance, the legal materials 414 may include a class-action lawsuit filed on behalf of patients that were harmed as a result of a particular medication being prescribed.

In step 520, the extraction system 310 also extracts second information related to treatment outcomes from the second data source 420. For instance, the extraction system 310 may perform natural language processing of the medical records 422 to extract data from the records. The extracted second information related to treatment outcomes may be associated with, for example, medical treatments that are thought or shown to be effective and/or viable. For instance, the extraction system 310 may extract information from patient charts indicating that a particular medication or substance is prescribed for a particular illness (e.g., insulin for diabetes). In some embodiments, the second information related to treatment outcomes may be a list of treatments that have some possibility of being advised by the medical decision support system 135.

In step 530, the machine learning system 320 develops a classifier based on the extracted first and second information related to treatment outcomes. For instance, the machine learning system 320 may use AI algorithms to compare the treatment outcomes from the first and second information to generate a tool for classifying any proposed treatment. The machine learning system 320 may be supplied with known information and/or use manual review to gradually teach a classifier to categorize proposed treatments based on the extracted first and second information.

In step 540, the categorization system 330 categorizes one or more proposed treatments. For instance, the categorization system 330 may apply a classifier developed in step 530 to a proposed treatment. The categorization system 330 may use the classifier to distinguish between proposed treatments that are potentially harmful and those that are safe (or unknown). In one example, the classifier may be trained to identify a particular medication as being problematic under certain circumstances (e.g., when another medication is also prescribed, when the patient has certain conditions or test results, etc.). If the proposed treatment includes the medication, the categorization system 330 may identify the proposal as potentially harmful.

In step 550, the alerting system 340 provides an alert based on the categorization of one or more proposed treatments. For instance, the alerting system 340 may provide an alert to the client terminal 130 indicating that a proposed treatment has been categorized as potentially harmful. In some embodiments, the alerting system 340 may provide a list of treatments that could be proposed by the medical decision support system 135 and which were categorized as being potentially harmful.

The alerting process 500 provides the advantage of considering known information on a large scale to identify situations in which medical treatment advice may be dangerous to the patient and/or embarrassing to a practitioner or medical decision support service provider. The alerting process 500 provides an additional safeguard against medical advice that may be recently known to be harmful, but which information has not yet been completely or properly disseminated to all relevant parties. The alerting process 500 is further beneficial to refining a medical decision support system, such as MDSS 135.

A medical decision support system may be any system that provides an automated recommendation for a proposed medical treatment. An automated system of this type could potentially suffer from malfunctions or knowledge gaps that lead to ambiguous, erroneous, or even dangerous treatment proposals (each of these being "potentially harmful").

Figure 6:
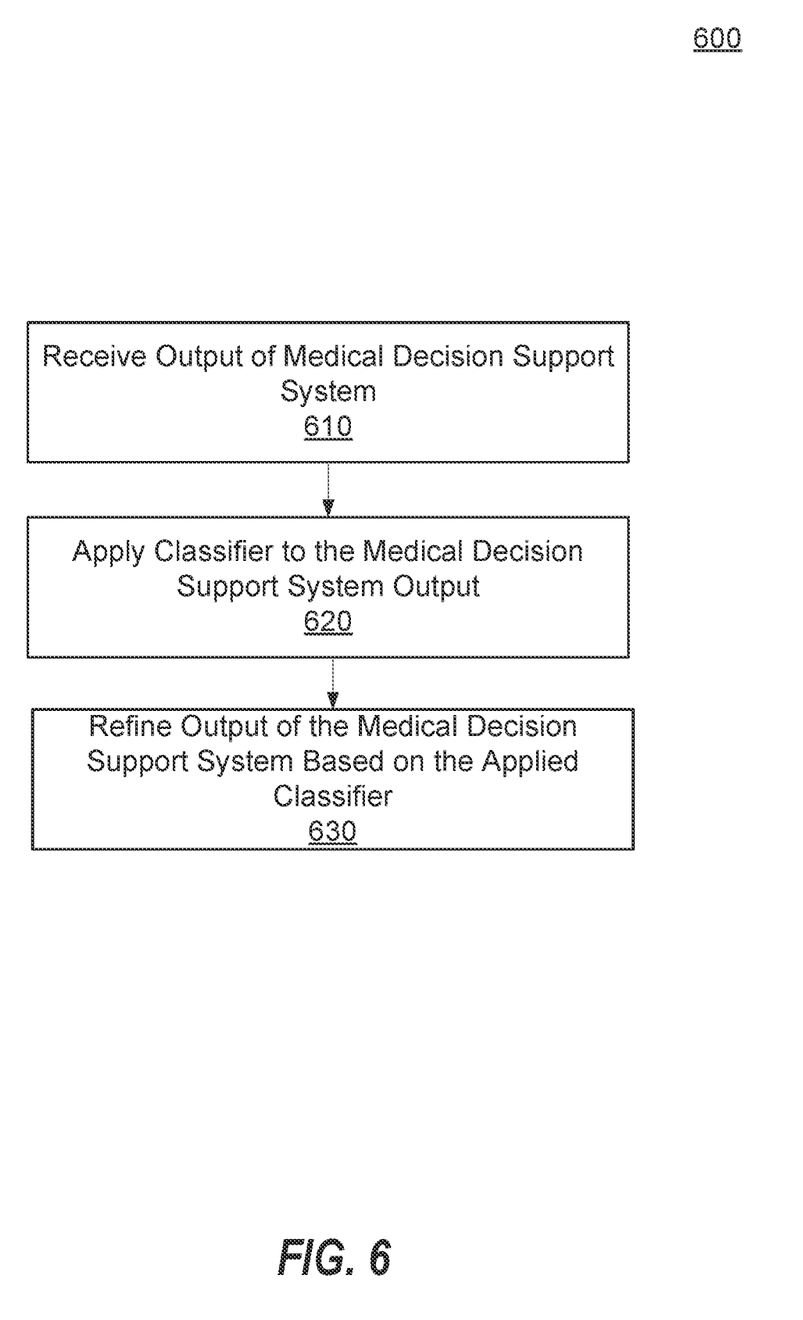
FIG. 6 is a flowchart of a decision support system learning process that may use aspects of the disclosed systems.

FIG. 6 is a flowchart of a process 600 for refining a medical decision support system, such as MDSS 135, that produces proposed treatments as part of its functioning. One or more of data analysis system 110 and client terminal 130 may perform one or more steps of the process 600 to improve a decisioning process of the medical decision support system and refine the potential treatment proposals that may be provided as output.

In step 610, the data analysis system 110 receives output of the MDSS 135. For instance, the output may include one or more proposed treatments that are or could be generated by the MDSS 135. The proposed treatments may involve medication, procedures, dietary advice, etc. The data analysis system 110 may receive the output of the MDSS 135 at the categorization system 330.

In step 620, the categorization system 330 applies a classifier to the output of the MDSS 135. The classifier in this case may be the same as the classifier developed by the machine learning system 320 in step 530 of process 500. The categorization system 330 thus may identify proposed treatments that are categorized as potentially harmful based on treatment outcome information extracted from the one or more data sources 120. For instance, the classifier may be trained based on an article indicating that insulin should not be given to certain patients (e.g., patients below a certain age, or of a certain ethnicity). If the MDSS 135 is not programmed to account for this issue, it is possible that the output of the MDSS 135 may suggest insulin be given to these patients. The categorization system 330 may categorize the proposed treatment may potentially harmful.

In step 630, the MDSS 135 may refine its processing and/or decisioning in order to account for the potentially harmful treatments identified in step 620. For instance, the data analysis system 110 may provide the categorized proposed treatments to the client terminal 130. In some embodiments, a user may receive the alert through the client terminal 130 and refine the MDSS 135 to account for the issue. In other embodiments, the MDSS 135 may use machine learning to refine its processing and/or decisioning. In this way, the MDSS 135 may be improved to account for known information that may not be otherwise incorporated into the decision process.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The system and processes of the Figures are not exclusive. Other systems, processes and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer-implemented method for alerting to ambiguous medical advice in a data processing system comprising a processing device and a memory comprising instructions which are executed by the processor, the method comprising:
    extracting first information related to negative outcomes of one or more medical treatments for a first disease of one or more patients from one or more first data sources, wherein the one or more patients are receiving another medical treatment for a second disease, wherein the one or more first data sources related to the negative outcomes include news articles and legal court cases related to the negative outcomes of the one or more medical treatments;
    extracting second information related to positive outcomes of the one or more medical treatments for the first disease from one or more second data sources;
    training a machine learning system by a training set including the first information and the second information to identify a negative treatment;
    applying the machine learning system to the extracted first information and second information to develop a classifier for categorizing proposed treatments for the first disease;
    producing, by the machine learning system, a list of treatments that are considered to be negative;
    comparing a proposed treatment for a particular patient having both the first disease and the second disease to the list of treatments;
    if the proposed treatment is on the list of treatments, categorizing the proposed treatment as being negative by the classifier, wherein the proposed treatment is provided while the particular patient is receiving another treatment for the second disease;
    if the proposed treatment is not on the list of treatments, categorizing the proposed treatment as being positive by the classifier, providing an alert to a client terminal regarding the proposed treatment.

2. The method of claim 1, wherein one or more first data sources comprises a corpus of documents comprising news sources, legal sources, and scientific sources.

3. The method of claim 1, wherein the one or more second data sources comprises medical records.

4. The method of claim 1, wherein the proposed treatment includes one or more of a prescribed medication, suggested procedure, or dietary advice.

5. The method of claim 1, wherein categorizing the proposed treatment based on the classifier includes determining a score for the proposed treatment and comparing the score to a threshold range.

6. The method of claim 1, wherein categorizing the proposed treatment based on the classifier includes comparing the proposed treatment to a list of treatments that are considered negative to determine whether there is a match.

7. The method of claim 1, further comprising receiving the proposed treatment from a medical decision support system.

8. The method of claim 7, further comprising refining the medical decision support system based on the categorization of the proposed treatment as being negative.

9. A data analysis system for alerting to ambiguous medical advice from a medical decision support system, comprising:
    an extraction system for extracting information related to negative outcomes of one or more medical treatments for a first disease of one or more patients from one or more publicly-available data sources, wherein the one or more patients are receiving another medical treatment for a second disease, wherein the one or more publicly-available data sources include news articles and legal court cases related to the negative outcomes of the one or more medical treatments;
    a machine learning system for developing a classifier based on the extracted information, producing a plurality of treatments that are considered to be negative, and comparing a proposed treatment for a particular patient having both the first disease and the second disease to the plurality of treatments;

a categorization system for categorizing, by the classifier, the proposed treatment for the first disease output from the medical decision support system for a particular patient having both the first disease and the second disease as being negative if the proposed treatment is one of the plurality of treatments; categorizing, by the classifier, the proposed treatment as being positive if the proposed treatment is different from any of the plurality of treatments; wherein the proposed treatment is provided while the particular patient is receiving another treatment for the second disease; and an alert system for providing alerts on proposed treatments that are categorized as being negative.

10. The data analysis system of claim 9, wherein the publicly-available data sources comprise news materials, legal materials, and scientific materials.

11. The data analysis system of claim 9, wherein the machine learning system uses a supervised learning algorithm to develop the classifier.

12. The data analysis system of claim 9, wherein the proposed treatments output from the medical decision support system include one or more of a prescribed medication, suggested procedure, or dietary advice.

13. A computer-implemented method for alerting to negative medical advice in a data processing system comprising a processing device and a memory comprising instructions which are executed by the processor, the method comprising:

extracting first information related to negative outcomes of one or more medical treatments for a first disease of one or more patients from one or more publicly-available data sources, wherein the one or more patients are receiving another medical treatment for a second disease, wherein the one or more first data sources related to the negative outcomes include news articles and legal court cases related to the negative outcomes of the one or more medical treatments;

extracting second information related to positive outcomes of the one or more medical treatments for the first disease from one or more other data sources;

training a machine learning system by a training set including the first information and the second information to identify a negative treatment;

applying the machine learning system to the extracted first information and second information to develop a classifier for categorizing the one or more medical treatments for the first disease;

producing, by the machine learning system, a plurality of treatments that are considered to be negative;

comparing a proposed treatment for a particular patient having both the first disease and the second disease to the plurality of treatments;

receiving a proposed treatment from a medical decision support system; and if the proposed treatment is one of the plurality of treatments,
categorizing the proposed treatment as being negative by the classifier, wherein the proposed treatment is provided while the particular patient is receiving another treatment for the second disease;

if the proposed treatment is different from any of the plurality of treatments,
categorizing the proposed treatment as being positive by the classifier.

14. The method of claim 13, wherein:

the publicly-available data sources comprise a corpus of documents having news materials, legal materials, and scientific materials, and the other data sources comprise a database of medical records.

* * * * *